US006641821B1

(12) United States Patent
Collin et al.

(10) Patent No.: US 6,641,821 B1
(45) Date of Patent: *Nov. 4, 2003

(54) COSMETIC COMPOSITION COMPRISING A FILM-FORMING POLYMER, A POLY-ALPHA-OLEFIN AND A LIQUID FATTY PHASE

(75) Inventors: Nathalie Collin, Sceaux (FR); Maryline Yon, Paris (FR); Bertrand Piot, Paris (FR)

(73) Assignee: L'Oréal S.A., Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/386,522

(22) Filed: Aug. 31, 1999

(30) Foreign Application Priority Data

Sep. 4, 1998 (FR) .............................................. 98 11101

(51) Int. Cl.$^7$ .......................... A61K 7/00; A61K 7/021; A61K 7/06
(52) U.S. Cl. ..................... 424/401; 424/70.1; 424/70.9; 424/70.12; 424/70.15; 424/70.16
(58) Field of Search ........................ 424/401, 63, 502, 424/70.1, 70.7, 70.9, 70.12, 70.15, 70.16

(56) References Cited

U.S. PATENT DOCUMENTS

| 3,734,874 A | | 5/1973 | Kibler et al. | |
|---|---|---|---|---|
| 3,937,811 A | | 2/1976 | Papantoniou et al. | |
| 4,060,569 A | | 11/1977 | Woods et al. | |
| 4,233,196 A | | 11/1980 | Sublett | |
| 4,239,546 A | | 12/1980 | Russell et al. | |
| 4,304,901 A | | 12/1981 | O'Neill et al. | |
| 4,536,405 A | * | 8/1985 | Nara et al. | 514/781 |
| 4,919,934 A | * | 4/1990 | Deckner et al. | 424/401 |
| 5,444,096 A | * | 8/1995 | McCrea et al. | 514/770 |
| 5,480,632 A | | 1/1996 | Orr et al. | |
| 5,556,613 A | | 9/1996 | Arnaud et al. | 424/64 |
| 5,725,845 A | | 3/1998 | Krog et al. | |
| 5,746,812 A | * | 5/1998 | Muller et al. | 106/10 |
| 5,750,095 A | | 5/1998 | Arnaud et al. | 424/64 |
| 5,849,318 A | * | 12/1998 | Imai et al. | |
| 5,925,337 A | * | 7/1999 | Arraudeau et al. | |
| 5,968,528 A | * | 10/1999 | Deckner et al. | |
| 6,180,123 B1 | * | 1/2001 | Mondet | 424/401 |
| 6,221,389 B1 | * | 4/2001 | Cannell et al. | 424/450 |
| 6,464,967 B1 | * | 10/2002 | Collin | 424/70.7 |

FOREIGN PATENT DOCUMENTS

| EP | 0 422 862 | 4/1991 |
|---|---|---|
| EP | 0 547 897 | 6/1993 |
| EP | 0 611 170 | 8/1994 |
| EP | 0 685 221 | 12/1995 |
| EP | 0 792 633 | 9/1997 |
| EP | 0 815 826 | 1/1998 |
| EP | 0 819 428 | 1/1998 |
| FR | 2 232 303 | 1/1975 |
| WO | WO 91/12793 | 9/1991 |
| WO | WO 95/15741 | 6/1995 |
| WO | WO 97/35542 | 10/1997 |

OTHER PUBLICATIONS

Hawley, The Condensed Chemical Dictionary, 1971, 8$^{th}$ Ed., pp. 706, 710.*
Encyclopedia of Chemical Technology, KIRK–OTHMER, vol. 22, 3$^{rd}$ Edition, 1979, pp. 333–432.
English language Derwent Abstract of EP 0 611 170.
English language Derwent Abstract of EP 0 685 221.
English language Derwent Abstract of EP 0 792 633.
English language Derwent Abstract of EP 0 815 826.
English language Derwent Abstract of EP 0 819 428.
English language Derwent Abstract of FR 2 232 303.

* cited by examiner

Primary Examiner—Sreeni Padmanabhan
Assistant Examiner—Gina C. Yu
(74) Attorney, Agent, or Firm—Finnegan, Henderson, Farabow, Garrett & Dunner, L.L.P.

(57) ABSTRACT

A cosmetic or dermatological film-forming composition comprising a liquid fatty phase, including at least one volatile hydrocarbon oil, and a film-forming polymer in said liquid fatty phase, characterized in that it comprises at least one polyolefin wax resulting from the polymerization of alpha-olefins having at least 10 carbon atoms, said wax having a melting point ranging from 50 to 80° C. The invention includes the use of such a composition, especially for producing a water-resistant film exhibiting good hold with regard to rubbing, to tears, to perspiration or to sebum.

51 Claims, No Drawings

COSMETIC COMPOSITION COMPRISING A FILM-FORMING POLYMER, A POLY-ALPHA-OLEFIN AND A LIQUID FATTY PHASE

The subject-matter of the present invention is a film-forming composition comprising a film-forming polymer, a volatile oil and a polyolefin wax intended in particular for the cosmetics and dermatological fields. More specifically, the invention relates to a composition for caring for and/or making up human skin, keratinous fibres (eyelashes, eyebrows or hair) or lips.

This composition can be provided in particular in the form of an eyeliner, mascara, make-up product for the body, concealer, eyeshadow, face powder, foundation, lipstick, sun protection composition, composition for colouring the skin, or styling product.

Products for making up or treating the skin are usually applied in the form of a thin uniform layer. For compositions intended for making up the edges of the eyelids, known as eyeliners, it is desirable for the film deposited after application to be resistant to water (waterproof), to tears, to perspiration and to sebum. In addition, it is desirable for the film to exhibit good hold with regard to rubbing with the fingers.

It is also desirable for the film deposited on the skin to have non-transfer properties, that is to say that it is not at least partially deposited and/or does not leave traces, on certain substrates with which the skin can be brought into contact, in particular an item of clothing or the skin.

For a water-resistant mascara, it is also desirable for the mascara deposited on the eyelashes to exhibit good hold, not to transfer onto the skin, for example during contact with the fingers or the edges of the eyes, and to resist rubbing with the fingers and tears.

The use is known, in conferring, on these compositions, good hold on the skin or on the eyelashes, of film-forming polymers dissolved in a medium composed of organic solvents and optionally waxes. Such a composition is disclosed in particular in U.S. Pat. No. 5,480,632.

However, when these film-forming compositions are fluid, they may not always exhibit good homogeneity over time and the consistency of the composition may not be uniform. This non-homogeneity is detrimental to the expected make-up properties and in particular does not make it possible to obtain a uniform make-up. In addition, a to thickening of the composition over time can sometimes be observed, rendering the latter difficult to apply to the skin or to the eyelashes.

The aim of the present invention is therefore to provide a film-forming composition which can exhibit good stability over time and can result in the formation of a homogeneous water-resistant film having good hold.

The inventors have found that the use of a specific polyolefin wax in a composition comprising a volatile oil and a film-forming polymer makes it possible to obtain a composition which can be completely stable and homogeneous over time and can result in the formation of a film exhibiting, in particular, good hold. The film obtained can in particular be highly resistant to water, to rubbing, to perspiration and to sebum; it can also exhibit good non-transfer properties.

A subject of the invention is therefore a cosmetic or dermatological film-forming composition comprising a liquid fatty phase, including at least one volatile hydrocarbon oil, and at least one film-forming polymer in the liquid fatty phase, characterized in that it comprises at least one polyolefin wax resulting from the polymerization of alpha-olefins having at least 10 carbon atoms, the at least one wax having a melting point ranging from 50 to 80° C.

Another subject of the invention is a process for making up or non-therapeutically treating the skin and/or keratinous fibres and/or lips comprising applying the composition according to the invention to the skin and/or keratinous fibres and/or lips.

Another subject of the invention is the use of the composition according to the invention for producing a water-resistant film.

A further subject of the invention is the use of the composition according to the invention for producing a film exhibiting good hold with regard to rubbing and/or to tears and/or to perspiration and/or to sebum.

Another subject of the invention is the use of the composition according to the invention for producing a film having non-transfer properties.

The invention also relates to the use of a polyolefin wax as defined above in a cosmetic or dermatological film-forming composition comprising a liquid fatty phase, including at least one volatile hydrocarbon oil, and a film-forming polymer which is soluble or dispersible in said liquid fatty phase for producing a homogeneous composition.

a) The Polyolefin Wax:

The polyolefin wax used in the composition according to the invention results from, the polymerization and in particular from the homopolymerization of an alpha-olefin corresponding to the general formula: $R-CH=CH_2$, in which R denotes an alkyl radical having at least 10 carbon atoms, preferably from 10 to 50 carbon atoms and more preferably from 25 to 50 carbon atoms. R is preferably a linear alkyl radical.

According to the invention, the term "homopolymerization of an alpha-olefin" is understood to mean the polymerization of monomers composed essentially of an alpha-olefin or a mixture of alpha-olefins as defined above.

The polyolefin wax preferably has a needle penetrability, measured at 44°C., ranging from 15 to 120, more preferably from 100 to 120 and better still from 105 to 115, determined as described below. The polyolefin wax preferably has a melting point ranging from 50° C. to 60° C.

Preferably, the polyolefin wax has a number-average molecular weight ranging from 400 to 3000, preferably from 2000 to 3000, and better still from 2500 to 2700.

Such polyolefin waxes are disclosed in U.S. Pat. No. 4,060,569 and 4,239,546, the disclosures of which are specifically incorporated by reference herein. These waxes are sold in particular under the name of "Performa V® 103", "Performa V® 253" and "Performa V® 260" by the company Petrolite.

These waxes exhibit the following characteristics:

|  | Performa V® 103 | Performa V® 253 | Performa V® 260 |
| --- | --- | --- | --- |
| Melting point (ASTM Standard D 36) | 74° C. | 67° C. | 54° C. |
| Number-average molecular weight | 2800 | 520 | 2600 |
| Polydispersity of the molecular weight | 6 | 8 | 11.5 |
| Density, measured | 0.92 g/cm³ | 0.92 g/cm³ | 0.90 g/cm³ |

-continued

|  | Performa V® 103 | Performa V® 253 | Performa V® 260 |
|---|---|---|---|
| at 25° C. (ASTM Standard D 792) |  |  |  |
| Hardness (needle penetrability-ASTM Standard D 1321) at 25° C. | 5 | 7 | 12 |
| Hardness (needle penetrability-ASTM Standard D 1321) at 44° C. | 20 | — | 110 |
| Viscosity at 99° C. (ASTM Standard D 3236) | 0.345 Pa · s (345 centipoises) | 0.006 Pa · s (6 centipoises) | 0.358 Pa · s (358 centipoises) |

The polydispersity of the molecular weight corresponds to the ratio of the weight-average molecular weight to the number-average molecular weight.

The needle penetrability of the waxes is determined according to French Standard NF T 60–123 or United States Standard ASTM D 1321 at a temperature of 44° C. According to these standards, the needle penetrability is a measurement of the depth, expressed in tenths of a millimeter, to which a standardized needle weighing 2.5 g, fitted into a mobile mounting weighing 97.5 g and placed on the test wax, penetrates into the wax over 5 seconds.

The polyolefin wax preferably has a density ranging from 0.85 to 0.95 g/cm$^3$.

The polyolefin wax can generally be present in the composition according to the invention in a content ranging from 0.1% to 10% by weight with respect to the total weight of the composition and preferably from 1% to 5% by weight.

b) The Liquid Fatty Phase:

The term "liquid fatty phase" is understood to mean, in the present invention, any non-aqueous medium which is liquid at room temperature. The term "volatile oil" is understood to mean an oil which can evaporate at room temperature from a substrate to which it has been applied, in other words an oil having a measurable vapour pressure at room temperature. The term "hydrocarbon oil" is understood to mean an oil comprising only hydrogen and carbon atoms.

The preferred volatile hydrocarbon oils suitable for the composition according to the invention are in particular isoparaffins, namely branched alkanes, comprising from 8 to 16 carbon atoms, such as "Isopars", Permetyls and in particular isododecane (also known as 2,2,4,4,6-pentamethylheptane). Mixtures of isoparaffins can, of course, also be used. Other volatile hydrocarbon oils, such as petroleum distillates, in particular those sold under the name Shell Solt by the company Shell, can also be used.

The volatile hydrocarbon oil can generally be present in the composition according to the invention in a content ranging from 20% to 99.4% by weight with respect to the total weight of the composition, preferably from 40% to 80% by weight and better still from 50% to 70% by weight.

The composition according to the invention can also comprise one or more additional volatile solvents other than the volatile hydrocarbon oils of the present invention. Representative additional volatile solvents include cyclic and volatile silicone oils, such as octamethylcyclotetrasiloxane, decamethylcyclopentasiloxane or hexadecamethylcyclohexasiloxane, volatile linear silicones, such as octamethyltrisiloxane, heptamethylhexyltrisiloxane or heptamethyloctyltrisiloxane, and volatile fluorinated oils, such as nonafluoromethoxybutane or perfluoromethylcyclopentane.

These additional volatile solvents preferably represent from 0 to 15% by weight of the volatile phase (in particular 0.1% to 15%).

The composition according to the invention can also comprise non-volatile oils and in particular non-volatile hydrocarbon and/or silicone and/or fluorinated oils.

Representative non-volatile hydrocarbon oils include:

hydrocarbon oils of animal origin, such as perhydrosqualene;

hydrocarbon oils of vegetable origin, such as liquid triglycerides of fatty acids comprising 4 to 10 carbon atoms, for example triglycerides of heptanoic or octanoic acids, sunflower, grape seed, sesame, maize, apricot, castor, avocado, olive, cereal germ, soybean, sweet almond, palm, rapeseed, cotton seed, hazelnut, macadamia or jojoba oils, triglycerides of caprylic/capric acids, such as those sold by the company Stéarineries Dubois or those sold under the names Miglyol 810, 812 and 818 by the company Dynamit Nobel, or karite butter oil;

linear or branched hydrocarbons of mineral or synthetic origin, such as liquid petrolatum, polydecenes or hydrogenated polyisobutene, such as parleam;

synthetic esters and ethers, such as oils of formula $R_{10}COOR_{11}$ in which $R_{10}$ represents the residue of a higher fatty acid comprising from 6 to 29 carbon atoms and $R_{11}$ represents a hydrocarbon chain comprising from 3 to 30 carbon atoms, such as purcellin oil, isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or 2-octyldodecyl lactate; or polyol esters, such as propylene glycol dioctanoate, neopentyl glycol diheptanoate, diethylene glycol diisononanoate and pentaerythritol esters;

fatty alcohols which are liquid at room temperature with a branched and/or unsaturated carbonaceous chain having from 12 to 26 carbon atoms, such as octyldodecanol, isostearyl alcohol, oleyl alcohol, 2-hexyldecanol, 2-butyloctanol or 2-undecylpentadecanol;

higher fatty acids, such as myristic acid, palmitic acid, stearic acid, behenic acid, oleic acid, linoleic acid, linolenic acid or isostearic acid; and their mixtures.

The non-volatile silicone oils which can be used in the composition according to the invention can be oils of low viscosity, such as linear polysiloxanes with a degree of polymerization preferably of 6 to 2000 approximately. Mention may be made, for example, of polydimethylsiloxanes (PDMS) with a viscosity of greater than 10 mPa·s, phenyl dimethicones, phenyl trimethicones, polyphenylmethylsiloxanes and their mixtures.

The non-volatile oils can be present in the composition according to the invention in a content ranging from 0% to 5% by weight (in particular 0.1% to 5%) with respect to the total weight of the composition, preferably from 0% to 2% by weight and better still from 0.1% to 2% by weight.

c) The Film-forming Polymer:

Preferably, the film-forming polymer which can be used in the composition of the present application is in particular soluble, i.e., fat-soluble, in the liquid fatty phase of the composition. Preferably, it can be present in the composition in a content ranging from 0.5% to 20% by weight with respect to the total weight of the composition and preferably from 1% to 15% by weight.

This film-forming polymer confers in particular good hold on the composition after application to the skin, keratinous fibres or lips.

The term "film-forming polymer" is understood to mean a polymer capable, alone, of forming an isolable film.

Mention may be made, by way of examples, of fat-soluble polymers, of the polymers corresponding to the following formula (I):

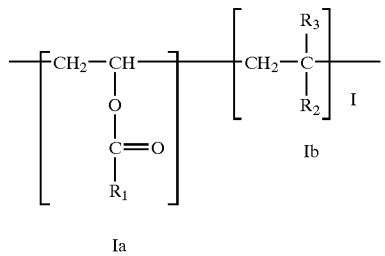

in which:
- $R_1$ is chosen from saturated, linear and branched, hydrocarbon chains having from 1 to 19 carbon atms;
- $R_2$ is a radical chosen from:
  a) —O—CO—$R_4$, $R_4$ having the same meaning as $R_1$ but being different from $R_1$ in the same copolymer,
  b) —$CH_2$—$R_5$, $R_5$ being chosen from saturated, linear and branched, hydrocarbon chains having from 5 to 25 carbon atoms,
  c) —O—$R_6$, $R_6$ being chosen from saturated hydrocarbon chains having from 2 to 18 carbon atoms, and
  d) —$CH_2$—O—CO—$R_7$, $R_7$ being chosen from saturated, linear and branched, hydrocarbon chains having from 1 to 19 carbon atoms,
- $R_3$ represents a hydrogen atom when $R_2$ represents the a), b) or c) radicals or $R_3$ represents a methyl radical when $R_2$ represents the d) radical, said copolymer being composed of at least 15% by weight of a unit (Ia) or a unit (Ib) in which said saturated or branched hydrocarbon chains have at least 7 carbon atoms.

The copolymers of formula (I) can result from the copolymerization of at least one vinyl ester (corresponding to the (Ia) unit) and of at least one other monomer (corresponding to the (Ib) unit) which can be an α-olefin, an alkyl vinyl ether or an allyl or methallyl ester.

When, in the (Ib) unit, $R_2$ is chosen from the —$CH_2$—$R_5$, —O—$R_6$ or —$CH_2$—O—CO—$R_7$ radicals as defined above, the copolymer of formula (I) can be composed of 50 to 95 mol % of at least one (Ia) unit and of 5 to 50 mol % of at least one (Ib) unit.

The copolymers of formula (I) can also result from the copolymerization of at least one vinyl ester and of at least one other vinyl ester different from the first. In this case, these copolymers can be composed of 10 to 90 mol % of at least one (Ia) unit and of 10 to 90 mol % of at least one (Ib) unit in which $R_2$ represents the —O—CO—$R_4$ radical.

Representative vinyl esters resulting in the unit of formula (Ia) or in the unit of formula (Ib) in which $R_2$=—O—CO—$R_4$, include vinyl acetate, vinyl propionate, vinyl butanoate, vinyl octanoate, vinyl decanoate, vinyl laurate, vinyl stearate, vinyl isostearate, vinyl 2,2-dimethyloctanoate and vinyl dimethylpropionate.

Representative α-olefins resulting in the unit of formula (Ib) in which $R_2$=—$CH_2$—$R_5$, include 1-octene, 1-dodecene, 1-octadecene, 1-eicosene and mixtures of α-olefins having from 22 to 28 carbon atoms.

Representative alkyl vinyl ethers resulting in the unit of formula (Ib) in which $R_2$=—O—$R_6$, include ethyl vinyl ether, n-butyl vinyl ether, isobutyl vinyl ether, decyl vinyl ether, dodecyl vinyl ether, cetyl vinyl ether and octadecyl vinyl ether.

Representative allyl or methallyl esters resulting in the unit of formula (Ib) in which $R_2$ =—$CH_2$—O—CO—$R_7$, include allyl and methallyl acetates, propionates, dimethylpropionates, butyrates, hexanoates, octanoates, decanoates, aurates, 2,2-dimethyl pentanoates, stearates and eicosanoates.

The copolymers of formula (I) can also be crosslinked using certain types of crosslinking agents to substantially increase their molecular weight.

This crosslinking is carried out during the copolymerization, and the crosslinking agents can either be of the vinyl type or of the allyl or methallyl type. Representative crosslinkers include tetraallyloxyethane, divinylbenzene, divinyl octanedioate, divinyl dodecanedioate and divinyl octadecanedioate.

Representative copolymers of formula (I) which can be used in the composition according to the invention, include: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% of divinylbenzene, vinyl dimethylpropionate/vinyl laurate, crosslinked with 0.2% of divinylbenzene, vinyl acetate/octadecyl vinyl ether, crosslinked with 0.2% of tetraallyloxyethane, vinyl acetate/allyl stearate, crosslinked with 0.2% of divinylbenzene, vinyl acetate/1-octadecene, crosslinked with 0.2% of divinylbenzene, and allyl propionate/allyl stearate, crosslinked with 0.2% of divinylbenzene.

Representative fat-soluble film-forming polymers include fat-soluble homopolymers and in particular those resulting from the homopolymerization of vinyl esters having from 9 to 22 carbon atoms or of alkyl acrylates or methacrylates, the alkyl radicals having from 10 to 20 carbon atoms.

Such fat-soluble homopolymers can be chosen from poly (vinyl stearate), poly(vinyl stearate) crosslinked using divinylbenzene, diallyl ether or diallyl phthalate, poly (stearyl (meth)acrylate), poly(vinyl laurate) or poly(lauryl (meth)acrylate), it being possible for these poly(meth) acrylates to be crosslinked using ethylene glycol or tetraethylene glycol dimethacrylate.

The fat-soluble copolymers and homopolymers defined above are known and are disclosed in particular in French Application Number 2,232,303, the disclosure of which is specifically incorporated by reference herein; they can have a weight-average molecular weight ranging from 2000 to 500,000 and preferably from 4000 to 200,000.

Representative fat-soluble film-forming polymers which can be used in the invention, include polyalkylenes and in particular copolymers of $C_2$–$C_{20}$ alkenes, other than the polyolefin wax defined in a), such as polybutene, alkylcelluloses with an alkyl radical chosen from saturated and unsaturated, linear and branched, $C_1$ to $C_8$ alkyl radicals, such as ethylcellulose and propylcellulose, or vinylpyrrolidone (VP) copolymers and in particular copolymers of vinylpyrrolidone and of a $C_2$ to $C_{40}$ alkene and better still a $C_3$ to $C_{20}$ alkene. Representative VP copolymers which can be used in the invention, include VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene, and VP/acrylic acid/lauryl methacrylate copolymers.

d) The Additives:

The fatty phase of the composition according to the invention can comprise, in addition to the volatile hydrocarbon oils and the polyolefin wax defined above, at least one wax chosen from waxes of animal, vegetable and synthetic origin.

The additional waxes capable of being used in the composition according to the invention generally possess a melting point of between 40 and 110°C., inclusive, and have a needle penetration at 25° C. of between 3 and 40, inclusive, as measured according to United States Standard ASTM D 5 or according to French Standard NFT 004. The principle of the measurement of penetration of a needle according to the ASTM D 5 and NFT 004 Standards consists in measuring the depth, expressed in tenths of a millimeter, to which a standardized needle which weighs 2.5 g, placed in a needle-holder weighing 47.5 g, i.e. a total of 50 g, penetrates, the needle being placed on the wax for 5 seconds.

Representative waxes of animal origin include beeswaxes, lanolin waxes and Chinese insect waxes.

Representative waxes of vegetable origin include rice waxes, carnauba, candelilla or ouricury waxes, cork fibre waxes, sugar cane waxes, japan waxes, sumach wax and cottonseed wax.

Representative waxes of mineral origin include paraffin waxes, microcrystalline waxes, montan waxes and ozokerites Preferred waxes of synthetic origin include polyethylene waxes, waxes obtained by the Fischer-Tropsch synthesis, waxy copolymers and their esters, and silicone waxes.

It is also possible to use hydrogenated oils of animal or vegetable origin which still correspond to the two physical characteristics mentioned above.

Representative hydrogenated oils include hydrogenated jojoba oils and hydrogenated oils which are obtained by catalytic hydrogenation of fatty substances comprising a chain chosen from linear and nonlinear $C_8$–$C_{32}$ fatty chains, hydrogenated sunflower oil, hydrogenated castor oil, hydrogenated coconut oil, hydrogenated lanolin and hydrogenated palm oils.

The waxes which can be used according to the present invention are preferably solid and stiff at a temperature of less than 50° C.

The composition according to the invention can generally comprise from 0% to 30% (in particular 0.1% to 30%) by weight of wax with respect to the total weight of the composition, preferably from 1% to 20% by weight and better still from 1% to 10% by weight.

The composition according to the invention can additionally comprise silicone gums. The silicone gums can be polysiloxanes with a high molecular mass, of the order of 200,000 to 1,000,000, having a viscosity of greater than 500,000 mPa·s. They can be used alone or as a mixture with a solvent, such as a polydimethylsiloxane or polyphenylsiloxane oil.

The gums can generally be present in the composition in a content ranging from 0% to 2% (in particular 0.1% to 2%) by weight with respect to the total weight of the composition, and preferably from 0.1% to 1% by weight.

The composition according to the invention can additionally comprise an agent for thickening the liquid fatty phase. The thickening agent can be chosen from organomodified clays, particularly those clays treated with compounds chosen from quaternary amines and tertiary amines. Representative organomodified clays include organomodified bentonites, such as those sold under the name "Bentone 34" by the company Rheox, or organomodified hectorites, such as those sold under the name "Bentone 27" or "Bentone 38" by the company Rheox.

The thickening agent can generally be present in a content ranging from 0.5% to 10% by weight with respect to the total weight of the composition and better still from 1% to 6% by weight.

The composition can also comprise at least one colouring material, such as pulverulent compounds and/or fat-soluble dyes, for example in a proportion of 0.01 to 30% of the total weight of the composition. The pulverulent compounds can be chosen from pigments, pearlescent agents and fillers commonly used in cosmetic or dermatological compositions. The pulverulent compounds generally represent from 0.1 to 25% of the total weight of the composition and preferably from 1 to 20%.

The pigments can be chosen from white and coloured, inorganic and organic pigments. Representative inorganic pigments include titanium dioxide, which is optionally surface treated, or zirconium or cerium oxides, as well as iron or chromium oxides, manganese violet, ultramarine blue, chromium hydrate and ferric blue. Representative organic pigments include carbon black, pigments of D & C type, and lakes based on cochineal carmine or on barium, strontium, calcium or aluminium.

The, pearlescent pigments can be chosen from white pearlescent pigments, such as mica covered with titanium oxide or with bismuth oxychloride, coloured pearlescent pigments, such as titanium dioxide-coated mica with iron oxides, titanium dioxide-coated mica with in particular ferric blue or chromium oxide, or titanium dioxide-coated mica with an organic pigment of the abovementioned type, and pearlescent pigments based on bismuth oxychloride.

The fillers can be chosen from those well-known to a person skilled in the art as commonly used in cosmetic compositions.

The composition can additionally comprise any additive generally used in such compositions, such as preservatives, fragrances, sunscreen agents, agents for combating free radicals, moisturizing agents, vitamins, proteins, ceramides or plasticizers.

Of course, a person skilled in the art will take care to choose this or these optional additional compounds and/or their amount so that the advantageous properties of the composition according to the invention are not, or not substantially, detrimentally affected by the envisaged addition.

The composition according to the invention is advantageously anhydrous and can comprise less than 10% by weight of water with respect to the total weight of the composition. The aqueous phase optionally present in the composition can comprise a cosmetically or dermatologically acceptable additive.

The composition according to the invention can be provided in the fluid, gel, semi-solid, supple paste or indeed even solid form, such as a stick. These pharmaceutical dosage forms are prepared according to the methods usual in the field under consideration.

The composition according to the invention can be used for making up or cosmetically treating the skin, keratinous fibres or lips. The make-up composition can be an eyeliner, a mascara, a foundation, an eyeshadow, a face powder, a lipstick, a concealer or a product for making up the body of the temporary or semi-permanent tattooing type. The cosmetic treatment composition can be a composition for caring for the face, neck, hands or body; it can also constitute an anti-sun or self-tanning composition.

The invention is illustrated in more detail in the following examples.

EXAMPLE 1

An eyeliner was prepared having the following composition:

| | |
|---|---|
| Waxes | 4.7% |
| Pigments | 11% |
| Thickening agent | 7% |
| Polyolefin wax (Performa V ® 260 from Petrolite) | 3.7% |
| Vinyl acetate/allyl stearate (65/35) copolymer (fat-soluble polymer) | 7.5% |
| Filler | 1% |
| Light naphthenic and paraffin hydrocarbons (Shell Solt from Shell) | 28.5% |
| Isoparaffin hydrocarbons (Isopar E from Esso) | 36.6% |

An eyeliner is obtained which is easily applied to the edge of the eyelids and leaves, after application, a homogeneous film exhibiting good hold over time with regard to water and to perspiration. The film does not deteriorate during the day.

EXAMPLE 2

A product for making up the body was prepared having the following composition:

| | |
|---|---|
| Polyolefin wax (Performa V ® 260 from Petrolite) | 3.7% |
| Vinylpyrrolidone/triacontene copolymer (Antaron WP-660 from Gaf) | 4% |
| Vinylpyrrolidone/eicosene copolymer (Antaron V-220 from Gaf) | 4% |
| Thickening agent | 7% |
| Filler | 1% |
| Pigments | 11% |
| Light naphthenic and paraffin hydrocarbons (Shell Solt from Shell) | 30% |
| Isoparaffin hydrocarbons (Isopar E from Esso) | 39.3% |

The composition is easily applied to the skin and leaves a film which has a good transfer-free property and which is resistant to rubbing with clothes and with the skin.

EXAMPLE 3

A mascara was prepared having the following composition:

| | |
|---|---|
| Polyethylene wax | 8% |
| Polyolefin wax (Performa V ® 260 from Petrolite) | 1% |
| Vinylpyrrolidone/triacontene copolymer (Antaron WP-660 from Gaf) | 3.5% |
| Vinylpyrrolidone/eicosene copolymer (Antaron V-220 from Gaf) | 3.5% |
| Thickening agent | 7% |
| Filler | 1% |
| Pigments | 11% |
| Light naphthenic and paraffin hydrocarbons (Shell Solt from Shell) | 28.5% |

| | |
|---|---|
| Isoparaffin hydrocarbons (Isopar E from Esso) | 36.5% |

The mascara is easily applied to the eyelashes and exhibits good hold throughout the day. The make-up obtained is homogeneous and resistant to water.

What is claimed is:

1. A cosmetic or dermatological film-forming composition, comprising:
    a liquid fatty phase, including at least one volatile hydrocarbon oil, and at least one film-forming polymer in said liquid fatty phase, and
    at least one polyolefin wax resulting from the homopolymerization of at least one alpha-olefin having at least 10 carbon atoms, and wherein said at least one polyolefin wax has a melting point ranging from 50° C. to 80° C.

2. The composition according to claim 1, wherein said at least one polyolefin wax has a melting point ranging from 50° C. to 60° C.

3. The composition according to claim 1, wherein said at least one polyolefin wax has a needle penetrability ranging from 15 to 120 when measured at 44° C. using the ASTM D 1321 or NF T 60–123 standard.

4. The composition according to claim 3, wherein said at least one polyolefin wax has a needle penetrability ranging from 100 to 120 when measured at 44° C. using the ASTM D 1321 or NF T 60-123 standard.

5. The composition according to claim 4, wherein said at least one polyolefin wax has a needle penetrability ranging from 105 to 115 when measured at 44° C. using the ASTM D 1321 or NF T 60-123 standard.

6. The composition according to claim 1, wherein said at least one polyolefin wax has a number-average molecular weight ranging from 400 to 3000.

7. The composition according to claim 6, wherein said at least one polyolefin wax has a number-average molecular weight ranging from 2000 to 3000.

8. The composition according to claim 7, wherein said at least one polyolefin wax has a number-average molecular weight ranging from 2500 to 2700.

9. The composition according to claim 1, wherein said at least one polyolefin wax has a density ranging from 0.85 to 0.95 g/cm$^3$ when measured at 25° C. using the ASTM Standard D 792.

10. The composition according to claim 1, wherein said at least one polyolefin wax is produced by homopolymerizing at least one alpha-olefin of formula: R—CH=CH$_2$, in which R is chosen from alkyl radicals having from 10 to 50 carbon atoms.

11. The composition according to claim 10, wherein R is chosen from alkyl radicals having from 25 to 50 carbon atoms.

12. The composition according to claim 11, wherein R is chosen from linear alkyl radicals.

13. The composition according to claim 1, wherein R is chosen from linear alkyl radicals.

14. The composition according to claim 1, wherein said at least one polyolefin wax is present in an amount ranging from 0.1% to 10% by weight with respect to the total weight of said composition.

15. The composition according to claim 14, wherein said at least one polyolefin wax is present in an amount ranging from 1% to 5% by weight with respect to the total weight of said composition.

16. The composition according to claim 1, wherein said at least one volatile hydrocarbon oil is chosen from isoparaffins having from 8 to 16 carbon atoms.

17. The composition according to claim 17, wherein said at least one volatile hydrocarbon oil is present in an amount ranging from 20% to 99.4% by weight with respect to the total weight of said composition.

18. The composition according to claim 17, wherein said at least one volatile hydrocarbon oil is present in an amount ranging from 40% to 80% by weight with respect to the total weight of said composition.

19. The composition according to claim 18, wherein said at least one volatile hydrocarbon oil is present in an amount ranging from 50% to 70% by weight with respect to the total weight of said composition.

20. The composition according to claim 1, wherein said liquid fatty phase further comprises at least one volatile solvent other than said at least one volatile hydrocarbon oil.

21. The composition according to claim 1, wherein said liquid fatty phase further comprises at least one non-volatile oil having an origin chosen from minerals, animals, vegetables and synthetic origins.

22. The composition according to claim 1, wherein said at least one film-forming polymer is soluble in the liquid fatty phase.

23. The composition according to claim 22, wherein said at least one film-forming polymer is chosen from copolymers of formula (I):

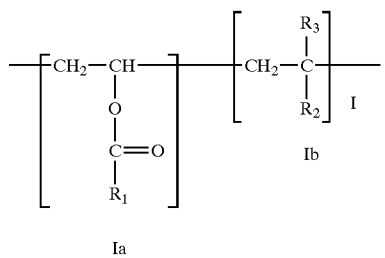

in which:
R$_1$ is chosen from saturated, linear and branched hydrocarbon chains having from 1 to 19 carbon atoms;
R$_2$ is a radical chosen from:
(a) —O—CO—R$_4$, in which R$_4$ is chosen from: saturated, linear and branched hydrocarbon chains having from 1 to 19 carbon atoms, with the proviso that R$_4$ is different from R$_1$ in the same copolymer;
(b) —CH$_2$—R$_5$, in which R$_5$ is chosen from: saturated, linear and branched, hydrocarbon chains having from 5 to 25 carbon atoms;
(c) —O—R$_6$, in which R$_6$ is chosen from: saturated hydrocarbon chains having from 2 to 18 carbon atoms; and
(d) —CH$_2$—O—CO—R$_7$, in which R$_7$ is chosen from saturated, linear and branched hydrocarbon chains having from 1 to 19 carbon atoms;
R$_3$ is a hydrogen atom when R$_2$ is a radical chosen from: —O—CO—R$_4$, —CH$_2$—R$_5$, and —O—R$_6$, or R$_3$ is a methyl radical when R$_2$ is a radical chosen from —CH$_2$—O—CO—R$_7$;
wherein said copolymer comprises at least 15% by weight of a unit (Ia) or a unit (Ib) in which said saturated or branched hydrocarbon chains have at least 7 carbon atoms.

24. The composition according to claim 22, wherein said at least one film-forming polymer is a homopolymer produced by homopolymerizing vinyl esters having from 9 to 22 carbon atoms or by homopolymerizing alkyl (meth) acrylates in which the alkyl radicals have from 10 to 20 carbon atoms.

25. The composition according to claim 22, wherein said at least one film-forming polymer is chosen from: copolymers of:
C$_2$–C$_{20}$ alkenes, but not including said at least one polyolefin wax;
alkylcelluloses with an alkyl radical chosen from saturated and unsaturated, linear and branched, C$_1$ to C$_8$ alkyl radicals; and
vinylpyrrolidone copolymers.

26. The composition according to claim 22, wherein said at least one film-forming polymer is chosen from: copolymers of vinylpyrrolidone and of C$_2$ to C$_{40}$ alkenes.

27. The composition according to claim 1 herein said at least one film-forming polymer is present in an amount ranging from 0.5% to 20% by weight with respect to the total weight of said composition.

28. The composition according to claim 27, wherein said at least one film-forming polymer is present in an amount ranging from 1% to 15% by weight with respect to the total weight of said composition.

29. The composition according to claim 1, further comprising at least one additional wax that is not said polyolefin wax and is of an origin chosen from: animals, vegetables and synthetic origins.

30. The composition according to claim 1, further comprising a silicone gum.

31. The cosmetic composition according to claim 1, further comprising at least one agent in an amount effective to thicken said liquid fatty phase.

32. The composition according to claim 1, further comprising at least one additive chosen from preservatives, fragrances, sunscreen agents, agents for combating free radicals, moisturizing agents, vitamins, proteins, ceramides and plasticizers.

33. The composition according to claim 1, wherein said composition is anhydrous.

34. A make-up, comprising a film-forming composition, which comprises:
a liquid fatty phase, including at least one volatile hydrocarbon oil, and at least one film-forming polymer in said liquid fatty phase, and
at least one polyolefin wax resulting from the homopolymerization of at least one alpha-olefin having at least 10 carbon atoms, and wherein said at least one polyolefin wax has a melting point ranging from 50° C. to 80° C.

35. An eyeliner, mascara, foundation, eyeshadow, face powder, lipstick, concealer or a temporary or semi-permanent tattooing product for making up the body, comprising a film-forming composition, which comprises:
a liquid fatty phase, including at least one volatile hydrocarbon oil, and at least one film-forming polymer in said liquid fatty phase, and
at least one polyolefin wax resulting from the homopolymerization of at least one alpha-olefin having at least 10 carbon atoms, and wherein said at least one polyolefin wax has a melting point ranging from 50° C. to 80° C.

36. A product for cosmetically treating skin, keratinous fibres or lips comprising a film-forming composition, which comprises:
a liquid fatty phase, including at least one volatile hydrocarbon oil, and at least one film-forming polymer in said liquid fatty phase, and at least one polyolefin wax resulting from the homopolymerization of at least one alpha-olefin having at least 10 carbon atoms, and wherein said at least one polyolefin wax has a melting point ranging from 50° C. to 80° C.

37. The product of claim 36, wherein said keratinous fibres are human keratinous fibres.

38. The product of claim 36, wherein said skin is on the face, neck, hands or body.

39. The product of claim 36, wherein said product is chosen from anti-sun and self-tanning products.

40. A process for making up the skin, keratinous fibres or lips, comprising:
applying to said skin, keratinous fibres or lips an effective amount of a film-forming composition, which comprises:
a liquid fatty phase, including at least one volatile hydrocarbon oil, and at least one film-forming polymer in said liquid fatty phase, and
at least one polyolefin wax resulting from the homopolymerization of at least one alpha-olefin having at least 10 carbon atoms, and wherein said at least one polyolefin wax has a melting point ranging from 50° C. to 80° C.

41. The process of claim 40, wherein said keratinous fibres are human keratinous fibres.

42. The process of claim 40, wherein said skin is on the face, neck, hands or body.

43. A process for non-therapeutically treating skin, keratinous fibres or lips, comprising:
applying to said skin, keratinous fibers or lips an effective amount of a film-forming composition, which comprises
a liquid fatty phase, including at least one volatile hydrocarbon oil, and at least one film-forming polymer in said liquid fatty phase, and
at least one polyolefin wax resulting from the homopolymerization of at least one alpha-olefin having at least 10 carbon atoms, and wherein said at least one polyolefin wax has a melting point ranging from 50° C. to 80° C.

44. A process for producing a film on the skin, keratinous fibres or lips, comprising:
applying to said skin, keratinous fibers or lips an effective amount of a film-forming composition, which comprises:
a liquid fatty phase, including at least one volatile hydrocarbon oil, and at least one film-forming polymer in said liquid fatty phase, and
at least one polyolefin wax resulting from the homopolymerization of at least one alpha-olefin having at least 10 carbon atoms, and wherein said at least one polyolefin wax has a melting point ranging from 50° C. to 80°°C., for a time sufficient to form a film having non-transfer properties.

45. A process for producing a film on the skin, keratinous fibres or lips, comprising:
applying to said skin, keratinous fibers or lips an effective amount of a film-forming composition, which comprises:
a liquid fatty phase, including at least one volatile hydrocarbon oil, and at least one film-forming polymer in said liquid fatty phase, and
at least one polyolefin wax resulting from the homopolymerization of at least one alpha-olefin having at least 10 carbon atoms, and wherein said at least one polyolefin wax has a melting point ranging from 50° C. to 80°°C., for a time sufficient to form a film having good hold with regard to rubbing and/or to tears and/or to perspiration and/or to sebum.

46. A process for producing a film on the skin, keratinous fibres or lips, comprising:
applying to said skin, keratinous fibers or lips an effective amount of a film-forming composition, which comprises:
a liquid fatty phase, including at least one volatile hydrocarbon oil, and at least one film-forming polymer in said liquid fatty phase, and
at least one polyolefin wax resulting from the homopolymerization of at least one alpha-olefin having at least 10 carbon atoms, and wherein said at least one polyolefin wax has a melting point ranging from 50° C. to 80°°C., for a time sufficient to form a film having water-resistant properties.

47. A homogeneous cosmetic or dermatological film-forming composition comprising:
a liquid fatty phase, including at least one volatile hydrocarbon oil, and at least one film-forming polymer soluble or dispersible in said liquid fatty phase, and at least one polyolefin wax resulting from the homopolymerization of at least one alpha-olefin having at least 10 carbon atoms, and wherein said at least one polyolefin wax has a melting point ranging from 50° C. to 80° C.

48. The composition according to claim 29, wherein said at least one additional wax is present in an amount ranging from 0.1% to 30% by weight with respect to the total weight of said composition.

49. The composition according to claim 48, wherein at least one additional wax is present in an amount ranging from 1% to 20% by weight with respect to the total weight of said composition.

50. The composition according to claim 1, further comprising at least one coloring material chosen from pulverulent compounds and fat-soluble dyes.

51. The composition according to claim 50, wherein said pulverulent compounds are chosen from pigments, pearlescent agents and fillers.

* * * * *

UNITED STATES PATENT AND TRADEMARK OFFICE
CERTIFICATE OF CORRECTION

PATENT NO. : 6,641,821 B1  
DATED : November 4, 2003  
INVENTOR(S) : Collin et al.

It is certified that error appears in the above-identified patent and that said Letters Patent is hereby corrected as shown below:

Column 10,  
Line 58, "claim 1," should read -- claim 10, --.

Column 11,  
Line 4, "claim 17," should read -- claim 1, --.

Column 12,  
Line 17, "claim 1 herein" should read -- claim 1, wherein --.  
Line 63, after "lips", insert a comma.

Column 13,  
Line 54, "80°°C.," should read -- 80°C., --.

Column 14,  
Lines 13 and 28, "80°°C.," should read -- 80°C., --.  
Line 44, after "wherein", insert -- said --.

Signed and Sealed this

Sixth Day of April, 2004

JON W. DUDAS  
*Acting Director of the United States Patent and Trademark Office*

UNITED STATES PATENT AND TRADEMARK OFFICE
CERTIFICATE OF CORRECTION

PATENT NO. : 6,641,821 B1
DATED : November 4, 2003
INVENTOR(S) : Collin et al.

It is certified that error appears in the above-identified patent and that said Letters Patent is hereby corrected as shown below:

Column 10,
Line 58, "claim 1," should read -- claim 10, --.

Column 11,
Line 4, "claim 17," should read -- claim 1, --.

Column 12,
Line 17, "claim 1 herein" should read -- claim 1, wherein --.
Line 63, after "lips", insert a comma.

Column 13,
Line 54, "80ººC.," should read -- 80ºC., --.

Column 14,
Lines 13 and 28, "80ººC.," should read -- 80ºC., --.
Line 44, after "wherein", insert -- said --.

Signed and Sealed this

Twenty-second Day of June, 2004

JON W. DUDAS
*Acting Director of the United States Patent and Trademark Office*